United States Patent [19]

Theobald et al.

[11] 4,320,122
[45] Mar. 16, 1982

[54] 6-FLUOROPYRIDYL-(di)(thio)PHOSPHORIC ACID ESTERS

[75] Inventors: Hans Theobald; Heinrich Adolphi, both of Limburgerhof; Karl Eicken, Wachenheim; Heinz-Guenter Oeser, Ludwigshafen, all of Fed. Rep. of Germany

[73] Assignee: BASF Aktiengesellschaft, Fed. Rep. of Germany

[21] Appl. No.: 154,753

[22] Filed: May 30, 1980

[30] Foreign Application Priority Data

Jun. 15, 1979 [DE] Fed. Rep. of Germany ....... 2924150

[51] Int. Cl.³ .................... A01N 57/08; C07F 9/58
[52] U.S. Cl. ....................................... 424/200; 546/25
[58] Field of Search .......................... 546/25; 424/200

[56] References Cited

U.S. PATENT DOCUMENTS

| | | | |
|---|---|---|---|
| 3,714,350 | 1/1973 | Gough | 546/25 |
| 3,810,902 | 5/1974 | Rigterink | 546/25 |
| 3,957,801 | 5/1976 | Drabek et al. | 546/25 |
| 4,223,025 | 9/1980 | Rigterink | 424/200 |
| 4,224,318 | 9/1980 | Pawloski | 424/200 |

Primary Examiner—Alan L. Rotman
Attorney, Agent, or Firm—Keil & Witherspoon

[57] ABSTRACT

6-Fluoropyridyl-(di)(thio)phosphoric acid esters, and their use for combating pests, especially from the classes of insects and Nemathelminthes.

The 6-fluoropyridyl-(di)(thio)phosphoric acid esters have the formula

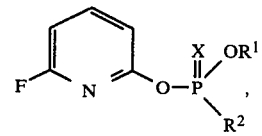

where X is oxygen or sulfur, $R^1$ is linear or branched alkyl of a maximum of 3 carbon atoms and $R^2$ is linear or branched alkylthio of a maximum of 6 carbon atoms.

8 Claims, No Drawings

6-FLUOROPYRIDYL-(di)(thio)PHOSPHORIC ACID ESTERS

The present invention relates to novel 6-fluoropyridyl-(di)(thio)phosphoric acid esters and a process for combating pests with these active ingredients.

It has been disclosed that O,O-dialkyl-O-halopyridyl-phosphoric acid is suitable for combating pests from the insect class (U.S. Pat. No. 3,928,370). It has also been disclosed that O,O-diethyl-O-(6-fluoropyrid-2-yl)-thiophosphate has a nematocidal action (U.S. Pat. No. 3,810,902).

We have found that 6-fluoropyridyl-(di)(thio)phosphoric acid esters of the formula

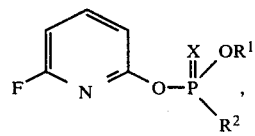

I where X is oxygen or sulfur, R$^1$ is linear or branched alkyl of a maximum of 3 carbon atoms and R$^2$ is linear or branched alkylthio of a maximum of 6 carbon atoms, combat pests from the classes of insects and nematodes more effectively than prior art halopyridylphosphoric acid derivatives.

Examples of linear or branched alkyl for R$^1$ in formula I are methyl, ethyl, n-propyl and isopropyl. Examples of linear or branched alkylthio for R$^2$ are methylthio, ethylthio, n-propylthio, isopropylthio, n-butylthio, isobutylthio, sec-butylthio, tert-butylthio, 3-methyl-n-butylthio, 2-methyl-n-butylthio, 4-methyl-n-pentylthio, 4-ethyl-n-butylthio and neopentylthio. Methyl and ethyl are particularly preferred for R$^1$ and propylthio and butylthio for R$^2$.

The 6-fluoropyridyl-(di)(thio)phosphoric acid esters of the formula I are obtained by reacting fluoropyridyl derivatives of the formula II with (di)(thio)phosphoric acid ester chlorides of the formula III in accordance with the following equation:

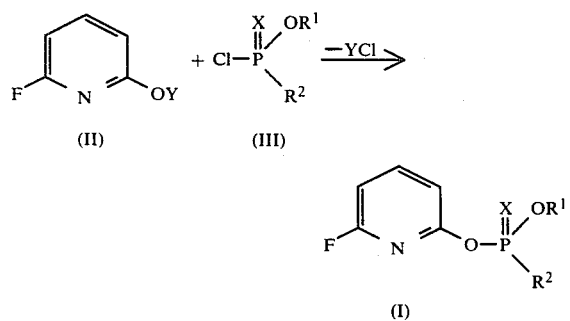

The radicals R$^1$, R$^2$ and X have the above meanings and Y denotes hydrogen, an alkali metal ion or one equivalent of an alkaline earth metal ion.

If 2-hydroxy-6-fluoropyridine is used, the hydrogen chloride evolved during the reaction may be removed for instance by blowing in an inert gas, e.g., nitrogen, or by adding a base. Examples of suitable bases are alkali metal and alkaline earth metal carbonates and hydroxides, alkali metal and alkaline earth metal bicarbonates, ammonia and unsubstituted or alkyl-substituted amines.

Generally, the reaction is carried out in solvents or diluents inert to the reactants. Suitable examples are water; ethers, such as tetrahydrofuran, dioxane, and diglycol dimethyl ether; ketones, such as acetone, methyl ethyl ketone, and diethyl ketone; aromatic hydrocarbons, such as toluene, xylenes, and chlorobenzenes; nitriles, such as acetonitrile; dimethylformamide; and dimethyl sulfoxide. Mixtures of these solvents or diluents may also be used. In some cases, it may be advantageous to add a phase transfer catalyst.

To carry out the process, the starting materials are usually used in equimolar amounts. In some instances, it may be advantageous to employ one of the reaction components in excess.

The reaction temperature may be varied within a wide range. Generally, the temperature is from 0° to 150° C., preferably from 20° and 100° C.

2-Hydroxy-6-fluoropyridine of the formula II which may be used as starting material may be prepared from 2,6-difluoropyridine (disclosed in Rec. trav. chim. Pays-Bas, 81, 1058, 1962). The (di)(thio)phosphoric acid ester chlorides of the formula III may be manufactured by conventional processes (Houben-Weyl, Methoden der organischen Chemie, 12/2, 621,755, Georg Thieme-Verlag, Stuttgart, 1964).

The following examples illustrate the preparation of the novel 6-fluoropyridyl-(di)(thio)phosphoric acid esters. Parts by weight bear the same relationship to parts by volume as kilograms to liters.

EXAMPLE 1

(compound no. 1)

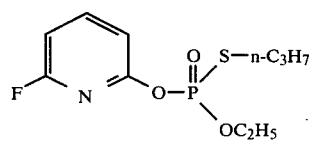

115 parts by weight of 2,6-difluorobenzene in 500 parts by volume of toluene is dripped, at 80° C., into 120 parts by volume of 50% strength aqueous sodium hydroxide solution. The reaction mixture is then stirred for 5 hours at 90° to 100° C. After the mixture has cooled, the toluene phase is separated off and the aqueous phase acidified with concentrated hydrochloric acid. Extraction is carried out with ether, and the ether phase is dried over sodium followed by filtration and concentration. The residue consists of 2-hydroxy-6-fluoropyridine; m.p.: 127°–130° C.

11.2 parts by weight of 2-hydroxy-6-fluoropyridine, 80 parts by volume of methanol and 18 parts by volume of a 30% strength sodium methylate solution are stirred for 1 hour at 50° C. The solvent is then removed in a rotary evaporator and the residue is taken up in 100 parts by volume of acetonitrile. 20.3 parts by weight of O-ethyl-S-n-propylphosphoric acid chloride is added and the resultant mixture is stirred for 7 hours at 60° C., followed by cooling, filtration and concentration. The oily residue is taken up in toluene and washed with 5% strength sodium bicarbonate solution and with water. After drying over sodium sulfate, concentration is carried out and the residue subjected to incipient distillation at 50° C./0.013 mbar. There is obtained 26.5 parts by weight of a pale yellow oil.

| | $C_{10}H_{15}NPO_3SF$ (279) | | | | | |
|---|---|---|---|---|---|---|
| | C | H | N | S | P | F |
| calc.: | 43.0 | 5.4 | 5.0 | 11.5 | 11.1 | 6.8 |
| found: | 43.3 | 5.6 | 5.5 | 11.8 | 10.7 | 6.6 |

220 MHz nmr spectrum (CDCl$_3$, δ values): 0.95 (3H); 1.4 (3H); 1.78 (2H); 3.02 (2H); 4.38 (2H); 6.82 (1H); 6.98 (1H); 7.9 (1H).

The (di)(thio)phosphoric acid esters of the formula I in the table below may be prepared analogously:

| Compound no. | X | R$^1$ | R$^2$ | NMR data (in CDCl$_3$; δ values) |
|---|---|---|---|---|
| 2 | S | C$_2$H$_5$ | n-C$_3$H$_7$S | (220 MHz), 0.95 (3H); 1.38 (3H); 1.7 (2H); 3.1 (2H); 4.35 (2H); 6.82 (1H); 7.03 (1H); 7.9 (1H) |
| 3 | O | C$_2$H$_5$ | i-C$_4$H$_9$—S | (220 MHz), 0.98 (3H); 1.44 (3H); 1.98 (1H); 3.0 (2H); 4.5 (2H); 6.8 (1H); 7.1 (1H); 7.9 (1H); |
| 4 | O | C$_2$H$_5$ | sec-C$_4$H$_9$—S | (220 MHz), 0.95 (3H); 1.3–1.5 (3H + 3H); 1.7 (2H); 3.5 (2H); 4.3 (2H); 6.8 (1H); 7.1 (1H); 7.85 (1H); |
| 5 | S | C$_2$H$_5$ | N(CH$_3$)$_2$ | (270 MHz), 1.4 (3H); 2.9 (6H); 4.2 (2H); 6.75 (1H); 6.9 (1H); 7.8 (1H); |
| 6 | S | C$_2$H$_5$ | NH(i-C$_3$H$_7$) | (270 MHz), 1.18 (6H); 1.37 (3H); 3.6 (1H); 4.2 (2H); 6.75 (1H); 7.05 (1H); 7.84 (1H) |

The 6-fluoropyridyl-(di)(thio)phosphoric acid esters of the formula I are suitable for effectively combating pests from the classes of insects and Nemetheliminthes. They may be used for crop protection, and in the hygiene, stores protection and veterinary sectors.

Examples of injurious insects from Lepidoptera order are *Plutella maculipennis, Leucoptera coffeella, Hyponomeuta malinellus, Argyresthia conjugella, Sitotroga cerealella, Phthorimaea operculella, Cupa reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar, Lymantria monocha, Pieris brassicae,* and *Aporia crataegi;*

Examples from the Coleoptera order are *Blitophaga undata, Melanotus communis, Limonius californicus, Agriotes lineatus, Agricotes obscurus, Agrilus sinuatus, Meligethes aenus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotetra nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Dipter order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitat, Rhagoletis cerasi, Rhagoletis pomonella, Anastrepha ludens, Oscinella frit, Phorbia coarctata, Phorbia antiqua, Phoria brassicae,* and *Pegomya hyoscyami;* examples from the Hymenoptera order are *Athalia rosae, Haplocampa minuta, Monomorium pharanois, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesema quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* an example from the Isoptera order is *Reticulitermes lucifugus.*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femurrubrum, Blatta orientalis, Blattella germanica, Periplaneta americana,* and *Blabera gigantea.*

Examples from the Nemathelminthes class are root-knot nematodes, e.g., *Meloidogyne incognita, Meloidogyne hapla,* and *meloidogyne javanica,* cyst-forming nematodes, e.g., *Heterodera rostochiensis, Heterodera scahachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratlenchus penetrans, Pratylenchus goodeyi, Paratylenchus curvitatus* and *Tylenechorhynchus dubius, Tylenechorhynchus claytoni, Roylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable aor animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples or surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 3 parts by weight of O-ethyl-S-n-propyl-O-(6-fluoropyrid-2-yl)-thiophosphate is intimately mixed with 97 parts by weight of particulate kaolin. A dust is obtained containing 3% by weight of the active ingredient.

II. 30 parts by weight of O-ethyl-S-isopropyl-O-(6-fluoropyrid-2-yl)-thiophosphate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of O-ethyl-S-n-propyl-O-(6-fluoropyrid-2-yl)-dithiophosphate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of O-ethyl-S-isobutyl-O-(6-fluoropyrid-2-yl)-phosphate is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active-ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 5%.

The active ingredients may also be successfully used in the ultra-low volume method, where it is possible to apply formulations containing more than 95% of active ingredient, or even the 100% active ingredient.

There may be added to the agents according to the invention (if desired, immediately before use (tankmix)) oils of various types, herbicides, fungicides, other insecticides, and bactericides. These agents may be added to the agents according to the invention in a ratio by weight of from 1:10 to 10:1.

Examples of active ingredients which may be admixed are as follows:

1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N',N'-dimethylformamide, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethylphosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioates, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)phosphorodithioate, O,O-diethyl-S-[6-chlorobenxoazolon-(2)-yl-(3)]-methyldithiophosphate, O,O-dimethyl-S-[2-methoxy-1,3,4-thiadiazol-5-onyl-(4)-methyl]-phsphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-n-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,transchrysanthemate, 5-benzylfuryl-(3)-methyl-DL-cis,trans-chrysanthemate, 3-phenoxybenzyl(±)-cis,-trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

The following examples demonstrate the biological action of the new compounds. The active ingredient

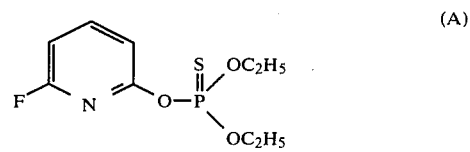

(A)

disclosed in U.S. Pat. No. 3,810,902 was used for comparison purposes. The remaining active ingredients are numbered as in the foregoing table.

EXAMPLE A

Contact action on cockroaches (*Blatta orientalis*)

The bottom of 1 liter preserving jars is lined with an acetonic solution of the active ingredients. After the solvent has evaporated, 5 adult cockroaches are introduced into each jar.

The kill rate is determined after 48 hours.

| Active ingredient no. | Amount of active ingredient per jar (mg) | Kill rate (%) |
| --- | --- | --- |
| 1 | 0.02 | 100 |
| 2 | 0.04 | 100 |
| 3 | 0.05 | 100 |
| 4 | 0.1 | 100 |
| A | 0.2 | 100 |
| A | 0.1 | <50 |

EXAMPLE B

Contact action on houseflies (*Musca domestica*)

1 μul of an acetonic solution of the active ingredients in administered by means of a microsyringe to the ventral abdomen of 4-day old imagoes under slight $CO_2$ narcosis.

20 identically treated animals are then introduced into a plastic bag (volume: about 500 ml). The flies in supine position are counted after 4 hours and the $LD_{50}$ is ascertained by means of a graph.

| Active ingredient no. | $LD_{50}$ (/ug/fly) |
| --- | --- |
| 1 | 0.055 |
| 2 | 0.12 |
| 3 | 0.04 |
| 5 | 0.165 |
| 6 | 0.08 |

EXAMPLE C

Contact action and effect of ingested food on caterpillars of the diamondback moth (*Plutella maculipennis*)

Leaves of young cabbage plants are dipped for 3 seconds in aqueous emulsions of the active ingredients and placed, after excess liquid has been briefly allowed to drip off, on a moist filter paper in a Petri dish. 10 caterpillars of the 4th stage are then placed on each leaf. The action is assessed after 48 hours.

| Active ingredient no. | Active ingredient concentration in emulsion (%) | Kill rate (%) |
|---|---|---|
| 1 | 0.002 | 100 |
| 2 | 0.002 | 80 |
| A | 0.004 | 80 |

EXAMPLE D

Contact action on bean aphids (*Aphis fabae*); spray experiment

Potted bean plants (*Vicia faba*) having large-sized aphid colonies are sprayed to runoff in a spray cabinet with aqueous formulations of the active ingredients. Evaluation takes place after 24 hours.

| Active ingredient no. | Active ingredient concentration in formulation (%) | Kill rate (%) |
|---|---|---|
| 1 | 0.01 | 100 |
| 2 | 0.01 | 100 |
| 3 | 0.001 | 80 |
| 4 | 0.025 | 100 |
| 5 | 0.01 | 100 |
| 6 | 0.02 | 100 |

EXAMPLE E

Contact action on granary weevils (*Sitophilus granarius*)

Petri dishes 10 cm in diameter are lined with acetonic solutions of the active ingredients. After the solvent has evaporated, 100 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

| Active ingredient no. | Amount of active ingredient per dish (mg) | Kill rate (%) |
|---|---|---|
| 1 | 0.02 | 100 |
| 2 | 0.2 | 100 |
| 2 | 0.1 | 80 |
| 3 | 0.04 | 100 |
| 4 | 0.04 | 80 |
| A | 0.2 | 100 |

-continued

| Active ingredient no. | Amount of active ingredient per dish (mg) | Kill rate (%) |
|---|---|---|
| A | 0.1 | <50 |

EXAMPLE F

Action on root-knot nematodes (*Meloidogyne incognita*)

300 g of a compost heavily infested with nematodes (*Meloidogyne incognita*) is intimately mixed with 30 ml of aqueous formulations of the active ingredients. Plastic pots 8 cm in diameter are filled with this compost and young tomato seedlings planted therewith. The plants are then kept for about 6 weeks under greenhouse conditions at a temperature of 24° C. The roots are subsequently assessed for cysts.

| Active ingredient no. | Concentration of active ingredient in soil (ppm) | |
|---|---|---|
| 2 | 25 | no cyst formation |
| 4 | 25 | " |
| 5 | 25 | " |
| 6 | 25 | " |

We claim:

1. A 6-fluoropyridyl-(di)(thio)phosphoric acid ester of the formula $$\begin{array}{c} \text{F} \diagup \!\!\!\diagdown \!\!\!\diagup \!\!\!\diagdown \\ \phantom{xx}\text{N} \phantom{xxx} \text{O}-\overset{\overset{\displaystyle X}{\|}}{\underset{\underset{\displaystyle R^2}{|}}{P}}-OR^1 \end{array} \quad \text{I}$$

where X is oxygen or sulfur, $R^1$ is linear or branched alkyl of a maximum of 3 carbon atoms, and $R^2$ is propylthio or butylthio.

2. O-ethyl-S-n-propyl-O-(6-fluoropyrid-2-yl)-thiophosphate.

3. O-ethyl-S-isobutyl-O-(6-fluoropyrid-2-yl)-phosphate.

4. A pesticidal composition comprising a solid or liquid carrier and an effective amount of 6-fluoropyridyl-(di)(thio)phosphoric acid ester of the formula I as claimed in claim 1.

5. A method for combating tests, wherein an effective amount of 6-fluoropyridyl-(di)(thio)phosphoric acid ester of the formula I as claimed in claim 1 is allowed to act on the pests or their habitat.

6. The process of claim 5, wherein said pests are *Blatta orientalis*.

7. The process of claim 5, wherein said pests are *Plutella maculipennis*.

8. The process of claim 5, wherein said pests are *Sitophilus granarius*.

* * * * *

UNITED STATES PATENT AND TRADEMARK OFFICE
CERTIFICATE OF CORRECTION

PATENT NO. :   4,320,122

DATED      :   March 16, 1982

INVENTOR(S):   Hans Theobald, Heinrich Adolphi, Karl Eicken
               and Heinz-Guenter Oeser It is certified that error appears in the above-identified patent and that said Letters Patent is hereby corrected as shown below:

Claim 5, first line, delete "tests" and insert --pests--.

*Signed and Sealed this*

*Twenty-second* Day of *November 1983*

[SEAL]

Attest:

GERALD J. MOSSINGHOFF

*Attesting Officer*   *Commissioner of Patents and Trademarks*